(12) United States Patent
Alpern et al.

(10) Patent No.: US 6,237,757 B1
(45) Date of Patent: *May 29, 2001

(54) HORIZONTAL DROP-FEED, DISPENSER BOX

(75) Inventors: Marvin Alpern, Glen Ridge; Michael Pohle, Flemington, both of NJ (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/400,238

(22) Filed: Sep. 21, 1999

(51) Int. Cl.$^7$ ...................................... A61B 17/06
(52) U.S. Cl. ..................... 206/63.3; 206/449; 229/122.1; 229/242
(58) Field of Search .................... 206/63.3, 449, 206/738; 229/120.15, 120.16, 122.1, 242

(56) References Cited

U.S. PATENT DOCUMENTS

| | | |
|---|---|---|
| D. 314,914 | 2/1991 | Callinan . |
| D. 322,905 | 1/1992 | Decker . |
| 4,834,242 | 5/1989 | Selack et al. . |
| 4,865,187 | 9/1989 | Zulauf et al. . |
| 5,143,210 | 9/1992 | Warwick et al. . |
| 5,148,972 | 9/1992 | Clayton . |
| 5,284,293 * | 2/1994 | Alpern et al. ...................... 229/122.1 |
| 5,375,700 | 12/1994 | Joss et al. . |
| 5,425,474 | 6/1995 | Dalea et al. . |
| 5,447,253 | 9/1995 | Williams . |
| 5,690,230 * | 11/1997 | Griffith ............................... 229/122.1 |
| 5,813,591 * | 9/1998 | Wakevainen ....................... 229/122.1 |
| 5,988,367 * | 11/1999 | Gemma .............................. 229/122.1 |

FOREIGN PATENT DOCUMENTS 0 819 408 A2    1/1998   (EP) .

* cited by examiner

Primary Examiner—Paul T. Sewell
Assistant Examiner—Shian Luong
(74) Attorney, Agent, or Firm—Emil Richard Skula

(57) ABSTRACT

A horizontal, drop-feed dispenser box for unitary surgical suture packages. The package allows for bottom or top dispensing of suture packages.

5 Claims, 8 Drawing Sheets

HORIZONTAL DROP-FEED, DISPENSER BOX

TECHNICAL FIELD

The field of art to which this invention pertains is packaging, in particular, packaging for surgical needles and sutures.

BACKGROUND OF THE INVENTION

Packages for surgical sutures and surgical needles are well known in the art. Typically, the sutures and needles are packaged in conventional unitary packages such as folder packages, or molded plastic trays. Such a package may contain multiple needles and sutures. These packages are then placed into outer wrap packages which are then sterilized. The sterilized packages are then placed into dispenser boxes. Dispenser boxes are boxes that are used to package multiple unitary suture packages. The boxes have features such that when the dispenser box is placed into a special holding rack, it is possible for the health care provider to easily remove the unit packages of sutures from the dispenser box as needed.

Although the existing dispenser boxes that are known in the art are useful for their intended purpose, there are also some disadvantages associated with their use. In particular, one disadvantage is that once unitary packages of sutures are removed from the box, and if they are not utilized during a procedure, it is often difficult to reinsert them into the dispenser box. In addition, in many conventional dispenser boxes it is not possible to have access to the unit suture packages from both the bottom of the dispenser box as well as the top of the dispenser box.

Accordingly, there is a need in this art for novel, improved dispenser boxes.

SUMMARY OF THE INVENTION

Accordingly, it is an object of the present invention to provide a novel suture package dispenser box which provides both bottom dispensing and top dispensing.

It is a further object of the present invention to provide a dispenser box which allows unitary suture packages to be easily reinserted into the dispenser box after removal.

Therefore, a dispenser box is disclosed. The dispenser box has a bottom panel, having opposed first and second major sides, and opposed first and second minor sides. A dispenser port closure panel having first and second opposed major sides and first and second opposed minor sides is foldably attached along the first major side to the second minor side of the bottom panel. A score line is located between the bottom panel and the dispenser port closure panel, said score line extending into the bottom panel to create semi-circular removal tabs. This score lines allows the closure panel to be separated from the bottom panel. A side panel having opposed first and second major sides and first and second minor sides is foldably connected along its second minor side to the first major side of the bottom panel. A dust flap panel is foldably connected to the first minor side of the side panel. A locking slot is located in the side panel, adjacent to the second minor side. A top panel having opposed first and second major sides and opposed first and second minor sides is provided. The top panel is foldably connected along a second minor side to a first major side of the side panel. A top access panel having opposed first and second major sides and opposed first and second minor sides is provided, wherein the top access panel is detachably connected along the first major side to the second major side of the top panel, and wherein the top access panel is detachably connected along the second minor side to the first major side of the side panel. A back panel is provided having opposed first and second major sides and opposed first and second minor sides, wherein the back panel is foldably connected along the second major side to the first major side of the top panel. A tuck flap having opposed first and second major sides is provided, wherein the tuck flap is foldably connected along its first major side to the first major side of the back panel. A front panel having opposed first and second major sides and opposed first and second minor sides is detachably connected by a score line along its first major side to the second major side of the top access panel, said score line forming at least one tab foldably connected to said first major side. The front base panel has opposed ends and tuck flap members foldably connected to each end. A second side panel having opposed first and second major sides and first and second minor sides is foldably connected along the first major side to the first minor side of the top panel and detachably connected to the first minor side of the top access panel. A dust flap is foldably connected to the second side panel along the first minor side of the panel. A locking slot is provided in the second side panel adjacent to the second minor side of the second side panel. A glue flap panel having opposed first and second major sides and first and second minor sides, is foldably connected along a first major side to the second major side of the second side panel, said glue flap panel has a cutout adjacent to the first minor end. A partition panel having first and second opposed major sides and first and second opposed minor sides is foldably connected along a first major side to the second major side of the glue flap panel. A glue flap is foldably connected along the second major side of the partition panel.

These and other aspects of the present invention will become more apparent from the following description and accompanying drawings.

BEST MODE FOR CARRYING OUT THE INVENTION

Figure 1:
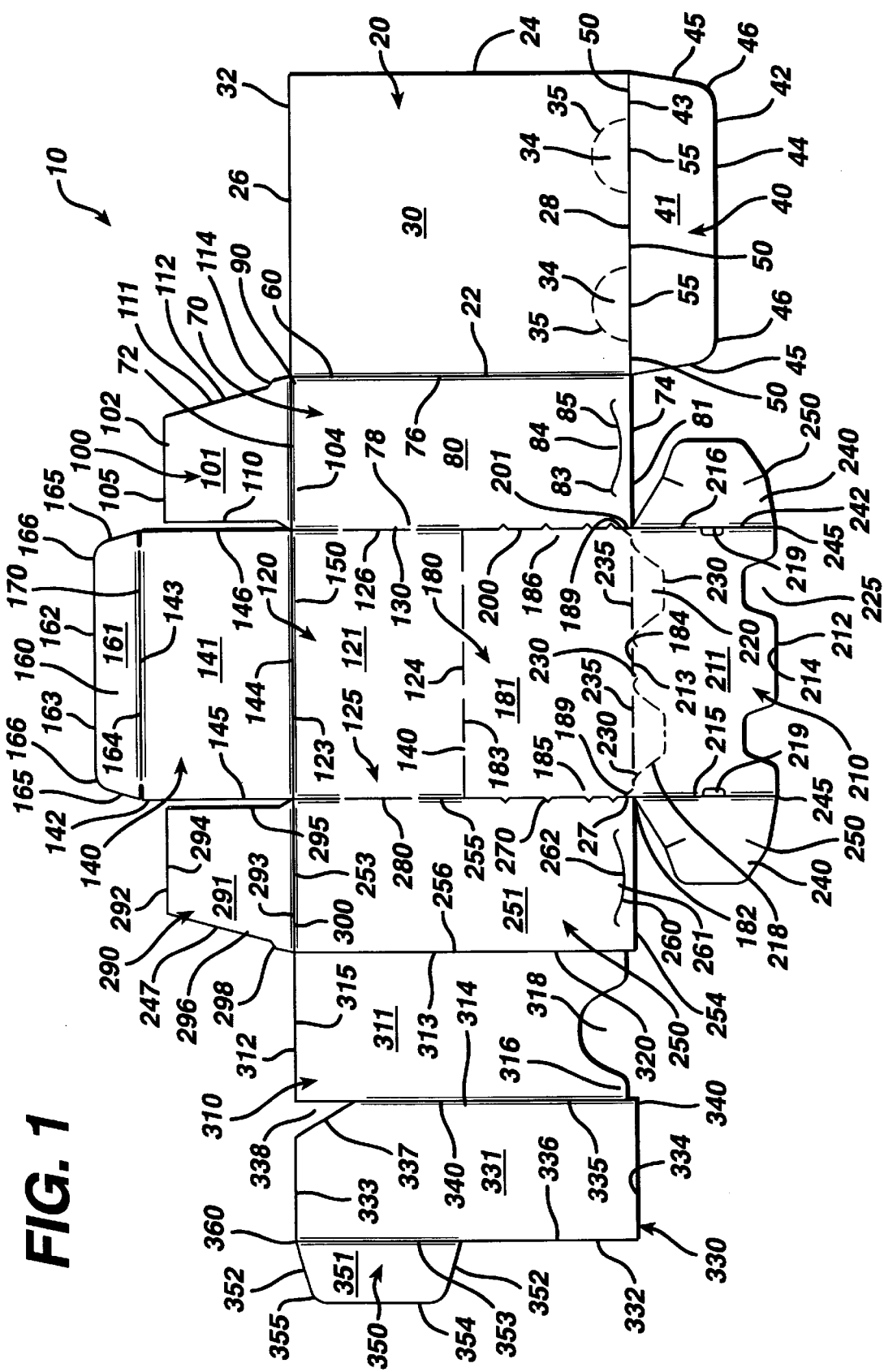
FIG. 1 is a plan view of a package of the present invention.
Figure 2:
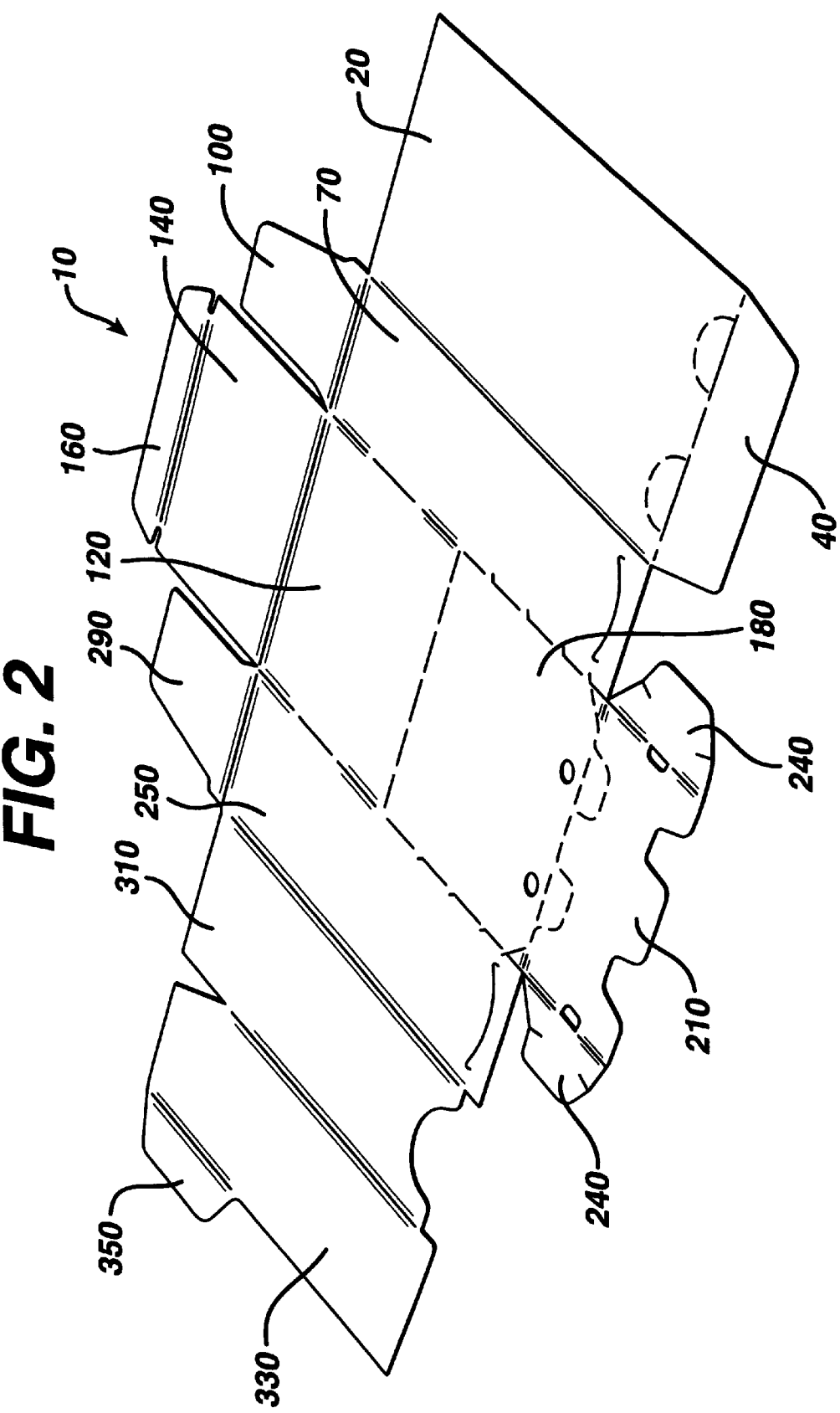
FIG. 2 is a perspective view of the package of FIG. 1 prior to folding and assembly.

Referring first to FIG. 1 and FIG. 2, the package 10 of the present invention is seen to be a folder-type package having a number of foldably connected panels, as well as several panels connected by score lines. The package 10 is seen to have bottom panel 20. Bottom panel 20 is seen to be a rectangularly shaped panel having first side 22 and opposed second side 24, and first minor side 26 and opposed second minor side 28. Bottom panel 20 is seen to have top 30 and bottom 32. A pair of scored removal tabs 34 is seen to be located along second minor side 28. Removal tabs 34 are seen to be formed by curved score lines 35, which are preferably curved but may have different shapes including rectangular, square, semi-circular, elliptical, combinations thereof and the like. The dispenser port closure panel 40 is seen to be a substantially rectangularly shaped panel having top 41 and bottom 42. The dispenser port closure panel 40 is seen to have first major side 43 and second opposed major side 44. First major side 43 and second major side 44 are seen to be connected by angulated opposed minor sides 45. The dispenser port closure panel is seen to have curved ends 46 connecting second major side 44 and minor sides 45. The first major side 43 of closure panel 40 is seen to be connected to the second minor side 28 of bottom panel 20 along score lines 50 and fold lines 55. Side panel 70 is seen to be a substantially rectangularly shaped panel. Side panel 70 is seen to have first major side 78 and opposed second major side 76, along with first minor side 72 and opposed second minor side 74. The second major side 76 of the side panel 70 is foldably connected to the first major side 22 of bottom panel 20 along fold line 60. Side panel 70 is seen to have top surface 80 and bottom surface 81. Contained in panel 70 adjacent to the second minor side 74 is the curved slit 83 forming tab 84 and tab pocket 85. Foldably connected to first minor side 72 of side panel 70 along fold line 90 is the first dust flap 100. First dust flap 100 is seen to have top surface 101 and bottom surface 102. First dust flap 100 is seen to have first side 104 and opposed second side 105. Opposed sides 110 and 111 are seen to connect first and second sides 105 and 104. Side 111 is seen to have angulated section 112 forming notch 114. The first major side 104 of dust flap 100 is connected to the first minor side 72 of side panel 70 along fold line 90.

Top panel 120 is seen to be a rectangularly shaped panel having top surface 121 and bottom surface 122. The top panel 120 is seen to have first major side 123 and opposed second major side 124. The panel 120 is also seen to have first minor side 125 and opposed second minor side 126. The second minor side 126 of top panel 120 is seen to be foldably connected to the first major side 78 of side panel 70 along fold line 130. Back panel 140 is seen to be a substantially rectangularly shaped panel having top surface 141 and bottom surface 142. Back panel 140 is seen to have first major side 143 and opposed second major side 144. Back panel 140 is also seen to have first minor side 145 and opposed second minor side 146. The second major side 144 of back panel 140 is foldably connected to the first major side 123 of top panel 120 along fold line 150. The tuck flap 160 is seen to have top surface 161 and bottom surface 162. Tuck flap 160 is also seen to have first major side 163 and opposed second major side 164. Tuck flap 160 is also seen to have opposed minor sides 165 which are angled from second major side 164 toward first major side 163. The tuck flap 160 is also seen to have curved ends 166 connecting first major side 163 with minor sides 165.

The second major side 164 of tuck flap 160 is seen to be foldably connected to the first major side 143 of back panel 140 along fold line 170.

Figure 8:
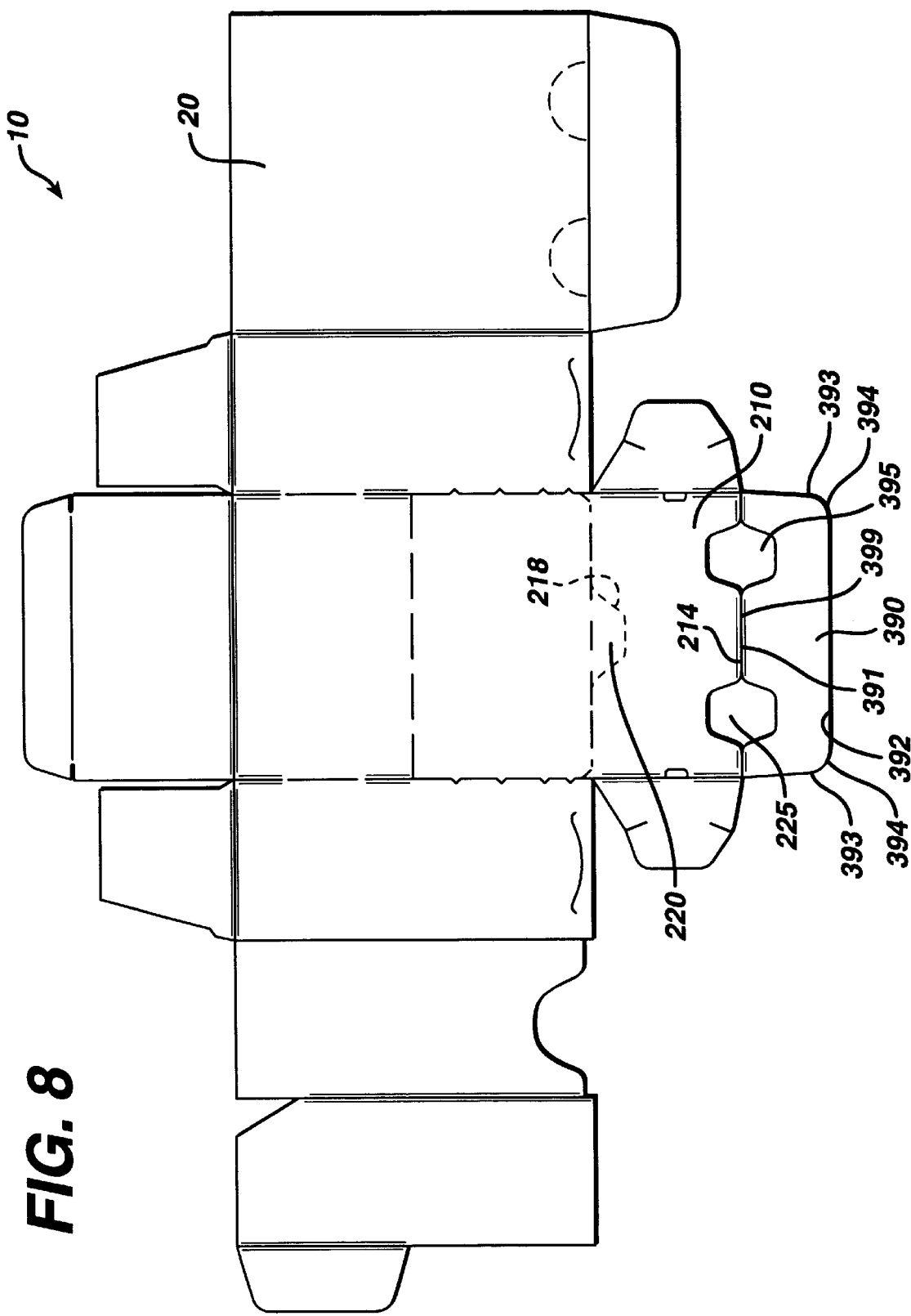
FIG. 8 is a top view of an alternate embodiment of a package of the present invention having a reinforcement panel foldably attached to the front panel; in addition, a single tab is contained in the front panel.

The top access panel 180 is seen to be a substantially rectangularly shaped panel having top surface 181 and bottom surface 182. The panel 180 is seen to have first major side 183 and opposed second major side 184. Panel 180 is also seen to have first minor side 185 and opposed minor side 186. The first major side 183 of access panel 180 is seen to be detachably connected to the second major side 124 of top panel 120 along score line 190. The second minor side 186 of panel 180 is seen to be detachably connected to the first major side 78 of side panel 70 along the score line 200, and foldably connected to a short section of first major side 78 along fold line 201. Front panel 210 is seen to be a substantially rectangularly shaped panel having top surface 211 and bottom surface 212. Front panel 210 is seen to have first major side 213 and opposed second major side 214. Front panel 210 is also seen to have score lines 218 creating tabs 220. In an alternate embodiment of the package 10 of the present invention as seen in FIG. 8, a single tab 220 is contained in panel 20 formed by a single score line 218. Front panel 210 is seen to be connected to the second major side 184 of top access panel 180 along score lines 230 and fold lines 235. The openings 225 are located along second major side 214 of panel 210. The angulated score lines 189 are seen in panel 180 along either end of first major side 184 to connect first major side 184 to first major side 78 of panel 70 and second major side 255 of panel 250, respectively. End flaps 240 are seen to be irregularly shaped panels having sides 242 foldably connected to first and second minor sides 215 and 216 of front panel 210, respectively, along fold lines 245. Each panel 240 is seen to have a pair of opposed slits 250. Adjacent to fold line 245 and contained in panel 210 are the site ports 219. Referring to FIG. 8, in an alternate embodiment of package 10, a reinforcement panel 390 may be foldably attached to the second major side 214 of panel 210. Panel 390 will be substantially a substantially rectangular panel having first major side 391, second opposed major side 392, and opposed minor sides 393 connecting the sides 391 and 392 at rounded corners 394. Openings 395 along major side 391 are mirror images of openings 225 in panel 210. The first major side 391 of panel 390 is foldably connected to the second major side 214 of panel 210 along fold line 399.

Side panel 250 is seen to be a substantially rectangularly shaped panel having top surface 251 and bottom surface 252. Side panel 250 is seen to have first minor side 253 and opposed second minor side 254. Panel 250 is also seen to have first major side 255 and opposed second major side 256. Contained in the panel 250 adjacent to the second minor side 254 is the slit 260 forming tab 261 and pocket 262. The first major side 255 of side panel 250 is connected to first minor side 125 of top panel 120 and first minor side 185 of top access panel 180 along score line 270, and fold line 280 and fold line 271, respectively. Second dust flap 290 is seen to have top surface 291 and bottom surface 292. Dust flap 290 is seen to have first side 293 and second opposed side 294, and also has third side 295 and opposed fourth side 296. Side 296 is seen to have angulated section 297 forming notch 298. The first side 293 of dust flap 290 is seen to be foldably connected to the first minor side 253 of side panel 250 along fold line 300. Glue flap panel 310 is seen to be a substantially rectangular panel having top surface 311 and bottom surface 312. Panel 310 is seen to have first minor side 315, second opposed minor side 316, first major side 313 and opposed major side 314. Flap 310 is seen to have semi-circular cutout 318 adjacent to second minor side 316. The first major side 313 of flap 310 is foldably connected to the second major side 256 of side panel 250 along fold line 320. Partition panel 330 is seen to be a substantially rectangular panel having opposed first and second major sides 335 and 336 respectively. Panel 330 also has opposed first and second minor sides 333 and 334 respectively. The panel 330 is seen to have top surface 331 and bottom surface 332. A portion of panel 333 adjacent to first minor side 333 is cut away to form triangular notch opening 338 along angulated side 337. The first major side 335 of panel 330 is foldably connected to the second major side 314 of panel 310 along fold line 340. The glue flap 350 is seen to have top surface 351 and bottom surface 352. Flap 350 is also seen to have first major side 353 and opposed second major side 354. Opposed angulated minor sides 352 are seen to connect first major side 353 with second major side 354. The panel 350 is also seen to have rounded corners 355. The glue flap panel 350 is foldably connected to panel 330 along fold line 362, such that the first major side 353 of panel 350 is adjacent to the second major side 336 of panel 330.

Figure 3:
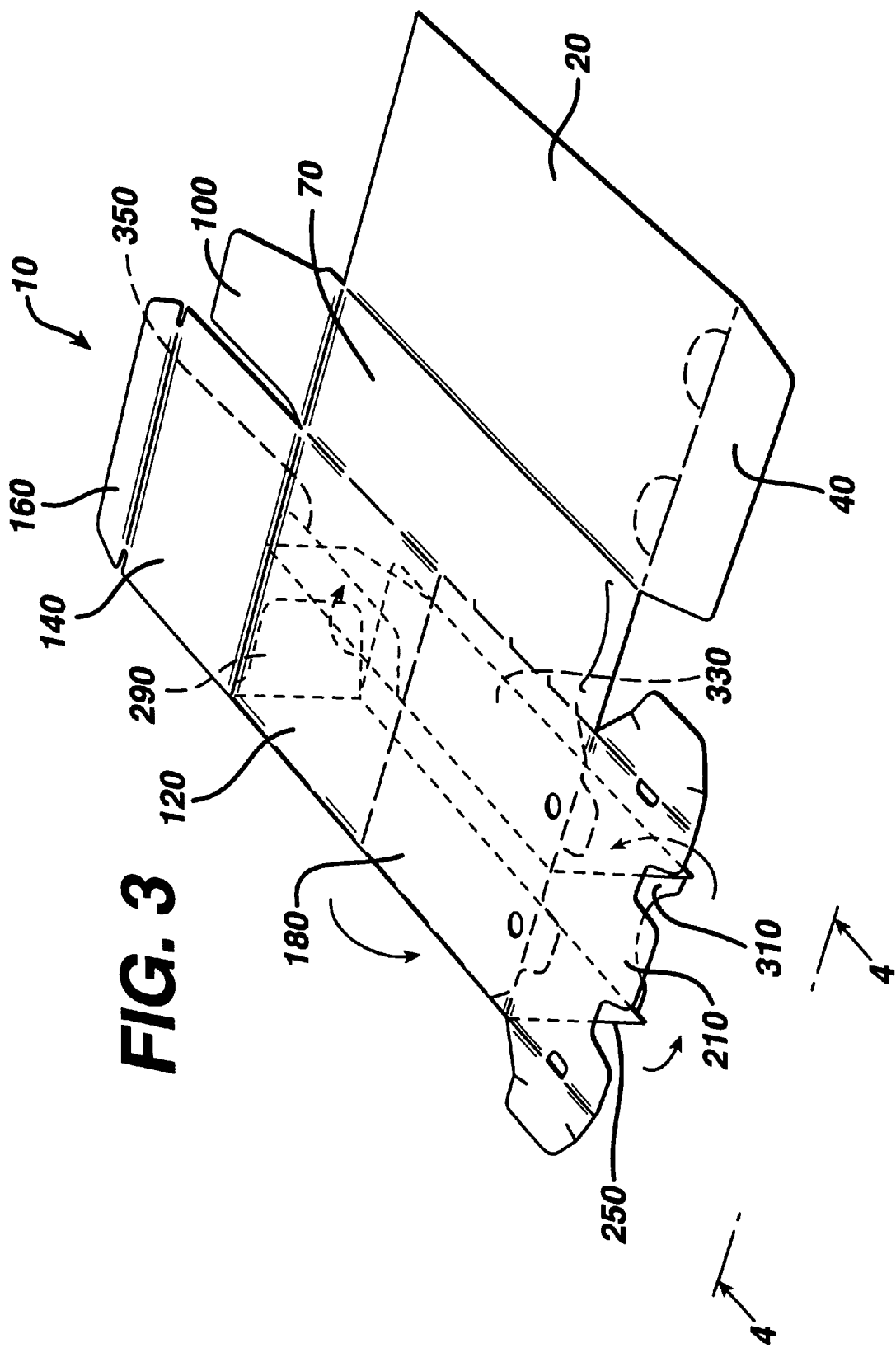
FIG. 3 illustrates the initial steps in the assembly of the package of the present invention.
Figure 4:
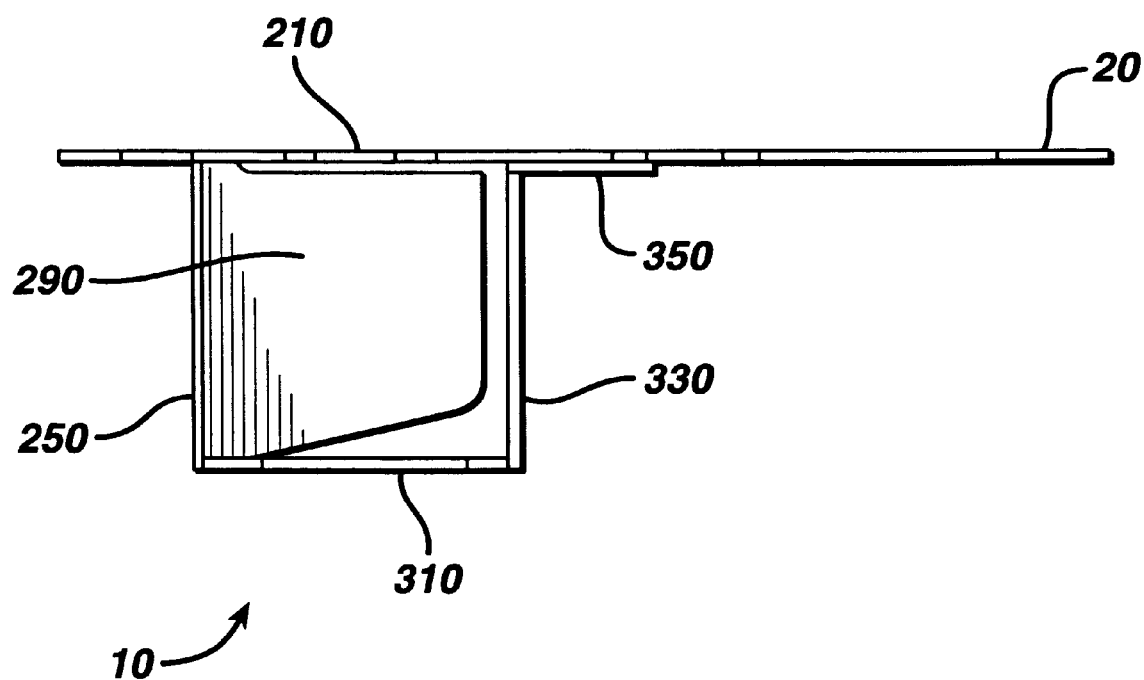
FIG. 4 is an end view taken along View Line 4—4 of the package of FIG. 3.
Figure 5:
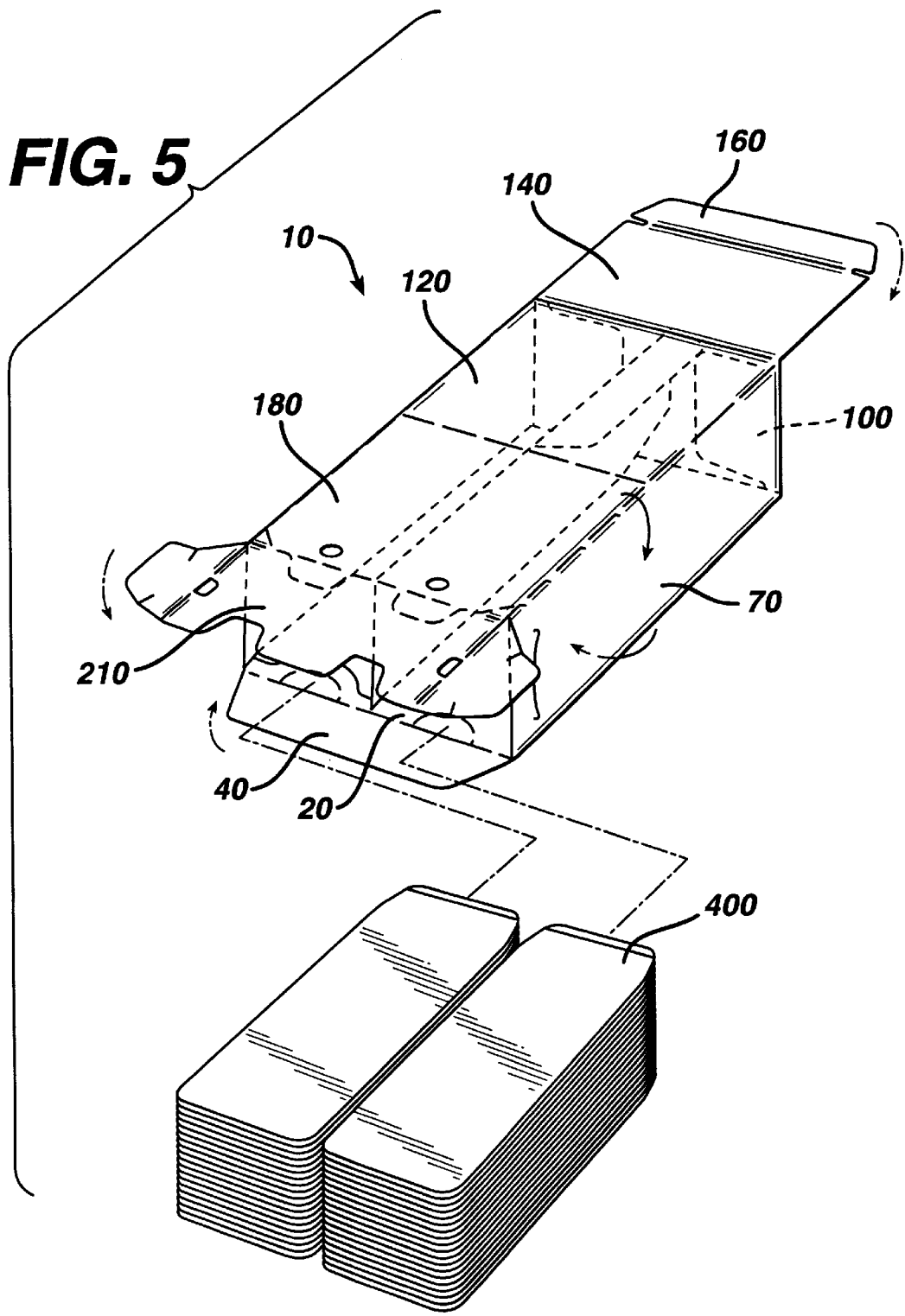
FIG. 5 is an illustration of the package of the present invention immediately prior to loading unitary suture packages.
Figure 6:
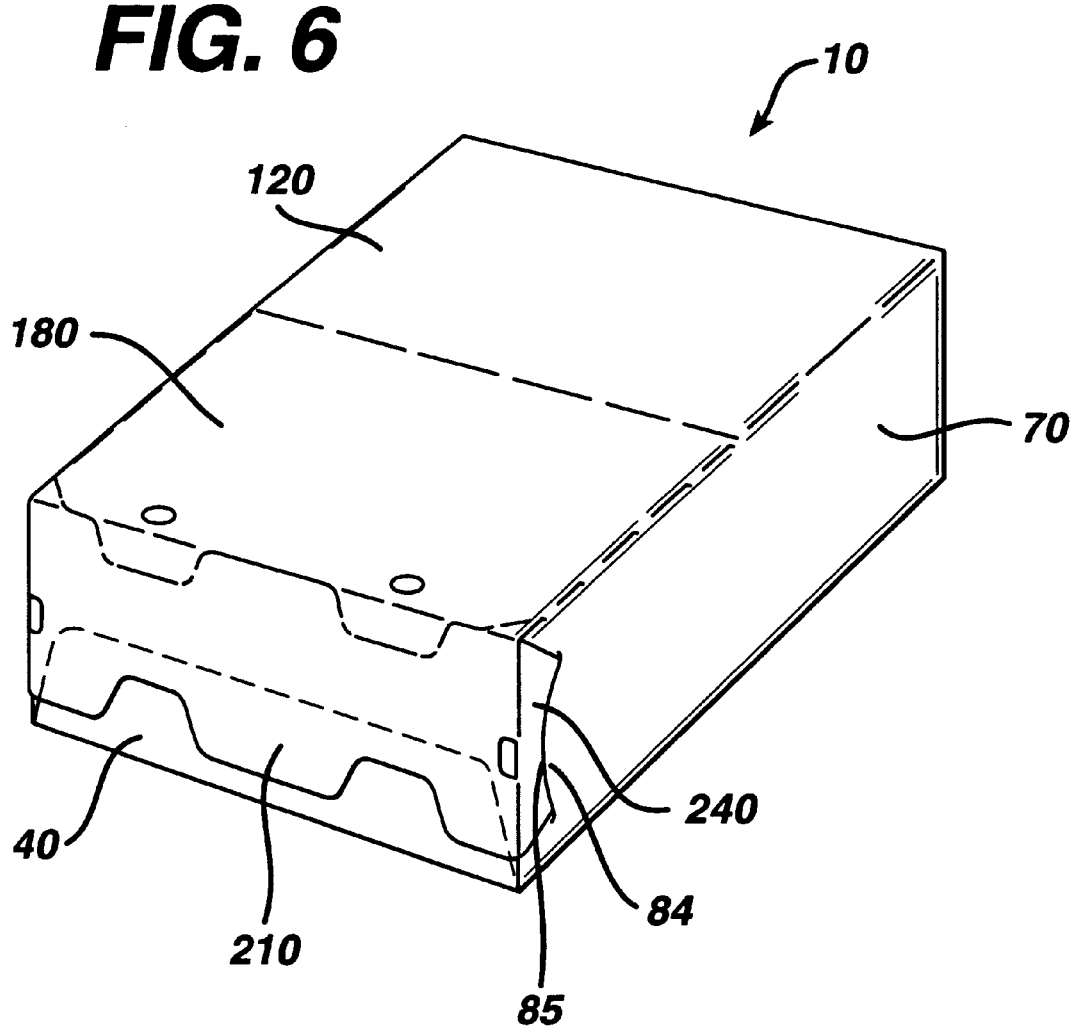
FIG. 6 is a perspective view of the package of the present invention after it has been fully assembled.

As seen in FIGS. 3, 4, and 5, the package of the present invention is assembled in the following manner. Side panel 250 is rotated downwardly (counter-clockwise) about score line 270 and fold line 280 such that side panel 250 is substantially perpendicular to top panel 120 and top access panel 180. Then glue flap panel 310 is rotated counter-clockwise around fold line 320 such that glue panel 310 is substantially perpendicular to side panel 250. Next, partition panel 330 is rotated counter-clockwise about fold line 340 until the partition panel 330 is substantially perpendicular to glue flap panel 310 and top access panel 180 and top panel 120.

Next, the glue flap 350 is rotated clockwise about fold line 360 such that the glue flap 350 is perpendicular to partition panel 330, and the flap panel 350 is also parallel to top panel 120. Then the top 351 of glue flap panel 350 is secured using a conventional glue or adhesive or fastener to the bottom 122 of top panel 120. If desired, tabs and tab pockets could be used to secure the glue flap. Next, the side panel 80 is rotated clockwise about fold line 130 and score line 200 such that the side panel 80 is substantially perpendicular to top access panel 180 and top panel 120. Next, the bottom panel 20 is rotated clockwise about fold line 60 such that the panel 30 is substantially perpendicular to side panel 80 and substantially parallel to glue flap panel 310 and top access panel 180 and top panel 120. Then the bottom 32 of panel 20 is glued to the top 311 of glue panel 310. Next, first and second dust flap panels 100 and 290 are folded inwardly about fold lines 90 and 300, respectively, such that dust flap 100 is substantially perpendicular to side panel 70 and dust flap panel 290 is substantially perpendicular to side panel 250. Then tuck flap 160 is rotated about fold line 170 such that tuck flap 160 is substantially perpendicular to back panel 140. Then back panel 140 is folded downward about fold line 150 and flap 160 is tucked beneath sides 110 and 297 of dust flap panels 100 and 290 respectively. At this point unit suture packages 400 may be loaded into the interior of the package 10. Once the package 10 is loaded with suture packages 400, the dispenser port closure panel 40 is folded upwardly about fold line 50 such that it is substantially perpendicular to bottom panel 20. Then the front panel 210 is rotated downwardly about score lines 230 and fold lines 235 such that it is substantially perpendicular to top access panel 180, and the bottom 212 of panel 210 is over the top 41 of dispenser port closure panel 40. Next, the end tabs 240 are rotated about fold lines 245 and the ends of the tabs 240 are inserted into tab pockets 85 and 262 on side panels 80 and 250, respectively.

Figure 7:
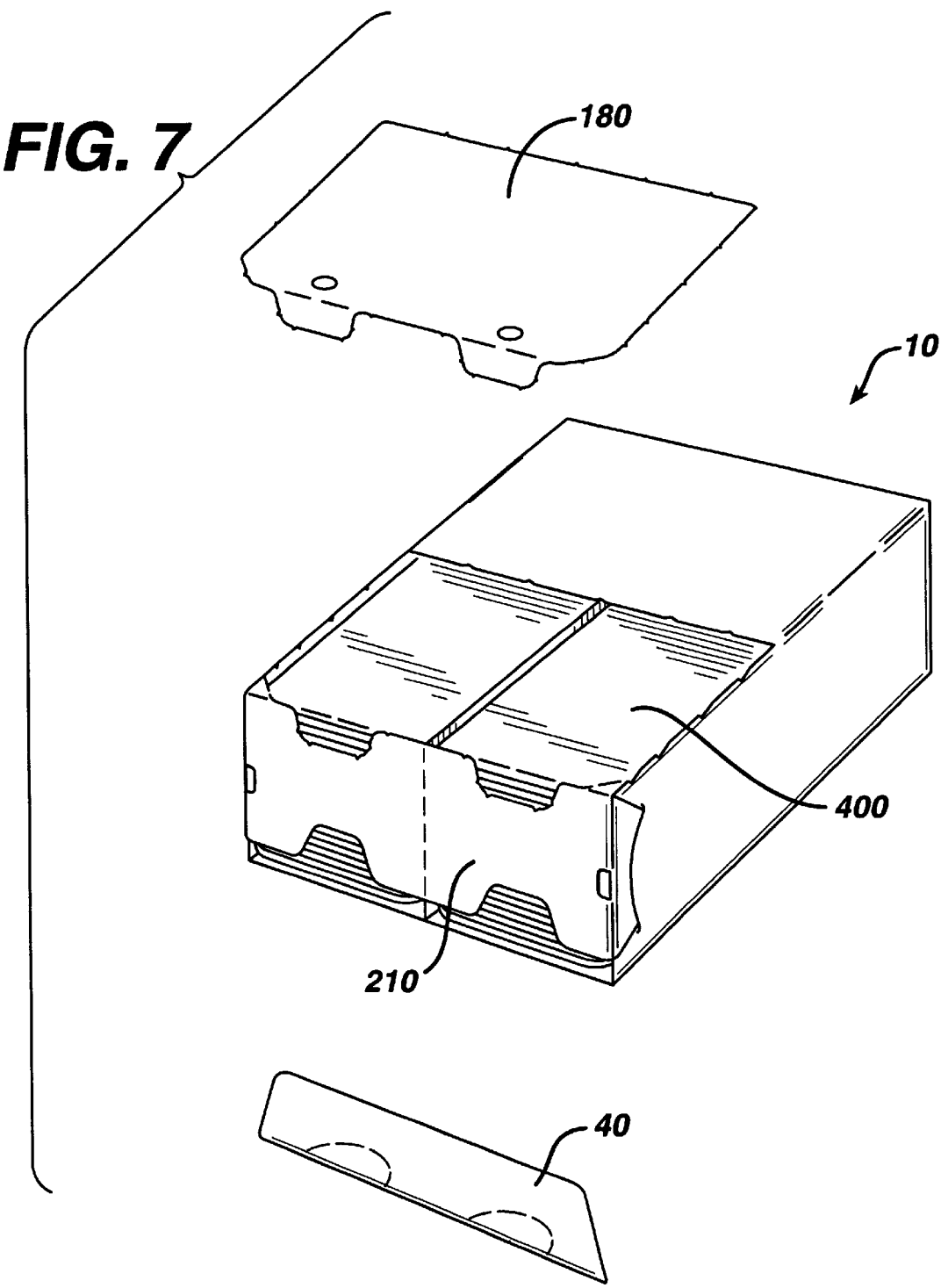
FIG. 7 is a perspective view of the package of FIG. 6 after the top access panel and the dispensing port closure panel have been removed to allow for bottom or top dispensing.

In order for the health care professional to access the unit suture packages 400 contained in a dispenser package 10 of the present invention, the dispenser port closure panel 40 is removed from the package 10 (see FIG. 7) along with the removal tabs 34 by pushing inward against the tabs 34 such that the tabs 34 are released from bottom panel 20 along score lines 35, and then pulling on dispenser port closure panel 40 such that it separates from top panel 20 along score lines 50. The sutures 400 are then ready for vertical dispensing and removal from opening 11. If top dispensing is also desired, the top access panel 180 is removed by first pressing inward on tabs 220 and causing them to separate from front panel 210 along score lines 218. Then, top access panel 180 is lifted upward causing it to separate from front panel 210, side panel 70, side panel 250 and top panel 120 along score lines 230, 200, 270 and 190, and 189, respectively.

It will be appreciated by those skilled in the art that the size of the packages 10 of the present invention and the sizes and shapes of the various panels and tabs will vary in accordance with the size of the suture anchor assembly and applicator. The package 10 and its associated panels and tabs will be of sufficient size to effectively contain a plurality of a particular unitary package of a suture or suture and surgical needle assembly as illustrated and described herein. If desired, the unitary packages may contain multiple sutures.

The packages 10 of the present invention are preferably constructed from any material having the required structural characteristics such that the material can be readily die cut, and scored. In addition, the material must be easily folded and sterilizable. The materials include those known in the art for packaging sutures and medical devices, including paper, plastic, foils, and laminates of one or more thereof. However, it is particularly preferred in the practice of the present invention to utilize a heavyweight, relatively stiff, medical grade paper or paperboard such as, for example, 0.007–0.016" suture board.

Although this invention has been shown and described with respect to detailed embodiments thereof, it will be understood by those skilled in the art that various changes in form and detail may be made without departing from the spirit and scope of the claimed invention.

What is claimed is:

1. A dispenser package for sutures, comprising:
    a bottom panel, having opposed first and second major sides, and opposed first and second minor sides;
    a dispenser port closure panel having first and second opposed major sides and first and second opposed minor sides, said closure panel foldably attached along the first major side to the second minor side of the bottom panel;
    a score line between the bottom panel and the dispenser port closure panel, said score line extending into the bottom panel to create semi-circular removal tabs, said score line allowing the closure panel to be separated from the bottom panel;
    a side panel having opposed first and second major sides and first and second minor sides, said panel foldably connected along the second major side to the first major side of the bottom panel;
    a dust flap panel foldably connected to the first minor side of the side panel;
    a locking slot in the side panel, adjacent to the second minor side;
    a top panel having opposed first and second major sides and opposed first and second minor sides, said top panel foldably connected along the second minor side to the first major side of the side panel;
    a top access panel having opposed first and second major sides and opposed first and second minor sides, wherein the top access panel is detachably connected along the first major side to the second major side of the top panel, and wherein the top access panel is detachably connected along the second minor side to the first major side of the side panel;

a back panel having opposed first and second major sides and opposed first and second minor sides, wherein the back panel is foldably connected along the second major side to the first major side of the top panel;

a tuck flap having opposed first and second major sides wherein the tuck flap is foldably connected along the first major side to the first major side of the back panel;

a front panel having a pair of opposed major sides and a pair of opposed minor sides, wherein a first major side is detachably connected to the second major side of the top access panel by a score line, wherein the front panel has opposed ends, and tuck flap members foldably connected to each end, wherein the score line forms removal tabs which are foldably connected to the second major side of the top access panel;

a second side panel having opposed first and second major sides and first and second minor sides, wherein the side panel is detachably connected along the first major side to the first minor side of the top access panel and foldably connected along the first minor side of the top panel;

a dust flap foldably connected to the second side panel along the first minor side of the dust panel;

a locking slot in the second side panel adjacent to the second minor side of the side panel;

a glue flap panel having opposed first and second major sides and first and second minor sides, wherein said glue flap panel is foldably connected along a first major side to the second major side of the second side panel, said glue flap panel having a cutout adjacent to the first minor end;

a partition panel having first and second opposed major sides and first and second opposed minor sides, said partition panel foldably connected along a first major side to the second major side of the glue flap panel; and a glue flap foldably connected along the second major side of the partition panel.

2. The package of claim 1 additionally comprising a plurality of unitary surgical suture packages.

3. The package of claim 1 additionally comprising at least one opening as a sight port in the front panel.

4. The package of claim 1 additionally comprising a reinforcing panel foldably attached to the front panel.

5. The package of claim 1 additionally comprising at least two removal tabs.

* * * * *